United States Patent [19]

Bodai et al.

[11] Patent Number: 4,929,426

[45] Date of Patent: May 29, 1990

[54] PORTABLE BLOOD CHEMISTRY MEASURING APPARATUS

[75] Inventors: Balazs I. Bodai, Sacramento; Michael D. Grandon, Sausalito; Scott J. Gilbert, Cupertino; Douglas J. Littlejohn, Sunnyvale; Kyle E. Lemons, San Jose; Richard L. Fellows, Mountain View; Michael R. Barry, Palo Alto; Michael D. Delapp, San Jose, all of Calif.

[73] Assignee: Biologix, Inc., Sacramento, Calif.

[21] Appl. No.: 266,474

[22] Filed: Nov. 2, 1988

Related U.S. Application Data

[62] Division of Ser. No. 115,714, Nov. 2, 1987.

[51] Int. Cl.$^5$ ............................................. G01N 35/06
[52] U.S. Cl. .......................................... 422/63; 422/98; 422/102; 422/104; 422/82.04; 422/82.02; 204/400; 204/409; 204/419; 204/435
[58] Field of Search ................... 422/63, 102, 104, 68, 422/98; 204/400, 408, 409, 416, 419, 433, 435

[56] References Cited

U.S. PATENT DOCUMENTS

| | | | |
|---|---|---|---|
| D. 269,548 | 6/1983 | Sarrine et al. | D24/19 |
| 3,467,582 | 9/1969 | Petersen | 204/1 |
| 3,556,950 | 1/1971 | Dahms | 204/1 |
| 3,638,109 | 1/1972 | Harnoncourt | 324/30 R |
| 3,648,159 | 3/1972 | Stansell | 324/30 R |
| 3,658,478 | 4/1972 | Spergel | 23/253 R |
| 3,897,216 | 7/1975 | Jones | 422/104 |
| 3,920,396 | 11/1975 | Schuy . | |
| 3,926,766 | 12/1975 | Niedrach et al. . | |
| 4,074,971 | 2/1978 | Braun et al. | 23/230 B |
| 4,083,638 | 4/1978 | Sandrock et al. | 356/246 |
| 4,152,390 | 5/1979 | Nosco et al. | 422/63 |
| 4,178,345 | 12/1979 | Terk | 422/61 |
| 4,187,077 | 2/1980 | Covington et al. | 422/104 |
| 4,190,420 | 2/1980 | Covington et al. | 422/104 |
| 4,214,968 | 7/1980 | Battaglia | 204/195 M |
| 4,257,862 | 3/1981 | Schnipelsky et al. | 422/63 |
| 4,272,245 | 6/1981 | Diamond et al. . | |
| 4,293,307 | 10/1981 | Simpson | 23/230 B |
| 4,301,116 | 11/1981 | Ida et al. | 422/63 |
| 4,312,734 | 1/1982 | Nichols | 204/195 G |
| 4,324,256 | 4/1982 | Vesterager | 128/635 |
| 4,336,121 | 6/1982 | Enzer | 204/195 R |
| 4,338,175 | 7/1982 | Binder et al. | 204/195 R |
| 4,339,317 | 7/1982 | Meiattini et al. . | |
| 4,340,457 | 7/1982 | Kater . | |
| 4,342,964 | 8/1982 | Diamond et al. . | |
| 4,397,725 | 8/1983 | Enzer | 204/406 |
| 4,401,547 | 8/1983 | Schinkmann | 204/415 |
| 4,436,610 | 3/1984 | Enzer | 204/400 |
| 4,452,682 | 6/1984 | Takata | 204/403 |
| 4,454,007 | 6/1984 | Pace | 204/1 T |
| 4,473,457 | 9/1984 | Columbus . | |
| 4,517,160 | 5/1985 | Galle et al. | 422/102 |
| 4,536,274 | 8/1985 | Papadakis | 204/433 |
| 4,545,382 | 10/1985 | Higgins et al. . | |
| 4,561,963 | 12/1985 | Owen et al. . | |
| 4,568,519 | 2/1986 | Hamilton et al. | 422/63 |
| 4,584,275 | 4/1986 | Okano et al. | 422/63 |
| 4,589,418 | 5/1986 | Gopikanth | 128/635 |
| 4,615,340 | 10/1986 | Cronenberg et al. . | |
| 4,662,996 | 5/1987 | Vekatasetty . | |
| 4,685,465 | 8/1987 | Klitgaard et al. . | |
| 4,695,430 | 9/1987 | Coville et al. | 422/102 |
| 4,738,824 | 4/1988 | Takeuchi | 422/104 |
| 4,761,268 | 8/1988 | Anderson et al. | 422/102 |
| 4,761,381 | 8/1988 | Blatt et al. . | |
| 4,764,342 | 8/1988 | Kelln et al. | 422/102 |

Primary Examiner—David L. Lacey
Assistant Examiner—Lou Ann Johnson
Attorney, Agent, or Firm—Limbach, Limbach & Sutton

[57] ABSTRACT

A portable apparatus for measuring the electrochemical characteristics of a sample is disclosed. A disposable cartridge, including a plurality of interconnected flow chambers, houses a printed circuit board substrate upon which reference and indicating electrodes are formed. The electrodes are employed in the presence of chemical reagents to aid in the electrochemical determination of a sample undergoing analysis. A thermal sensing element is in close proximity to the electrodes to permit the correction of the measurement for variations in temperature. After a pH value has been determined, the used cartridge can be mechanically ejected thus eliminating user exposure to the blood sample being measured. In this way, the pH of a blood sample can be determined quickly, effectively, inexpensively and with a minimum amount of sample and reagent preparation.

4 Claims, 5 Drawing Sheets

PORTABLE BLOOD CHEMISTRY MEASURING APPARATUS

This is a divisional of application Ser. No. 115,714, filed Nov. 2, 1987.

TECHNICAL FIELD

This invention relates to a portable apparatus to be used for accurately measuring the electrochemical properties of a given sample. More specifically, the present invention relates to an apparatus for measuring a blood gas panel, including pH value, of a whole blood sample.

BACKGROUND OF THE INVENTION

The pH value of blood is a commonly monitored metabolic parameter and provides a means for determining whether a proper physiological acid-base balance exists in the tested individual. A very delicate blood pH balance is present in humans. Normal values for arterial blood range from 7.25–7.45 with the lower and upper limits at which an individual can survive being 7.00 and 7.70, respectively. When a cardiac or medical arrest occurs, metabolic functions become anaerobic thus resulting in the production of excess acids. This causes blood pH to lower.

As medical practitioners are aware, accurate and rapid determination of whole blood pH promotes the safe and effective resuscitation and treatment of these arrest victims. Unfortunately, of the 640,000 cardiac arrests annually, 360,000 die before reaching the hospital partially due to improper blood pH levels which are incapable of being monitored on-site due to the prohibitory size of the current pH analyzers. Moreover, current analyzers are complex pieces of machinery requiring operation by skilled laboratory technicians. For example, calibration of these systems does not occur automatically. An electrolyte must be introduced into the measuring cassette by some form of mechanical manipulation before calibration can occur.

Additionally, the determination of pH on these systems is based on the glass electrode, as described by Cremer in 1906. These electrodes are composed of two half cells, one which generates a reference potential and the other being constructed of a glass membrane. These electrodes suffer from several shortcomings including the need for constant calibration as a result of half cell current drift, degradation of the membrane surface by cleaning solutions used to remove accumulated protein deposits, and the requirement of a large sample size.

U.S. Pat. No. 4,340,457 to Kater, discloses the use of metal electrodes to be used for in vivo potassium determination which can be stored wet in electrochemical contact. These electrodes, however, require further manipulation and hydration before calibration can occur. Further, the calibration liquid must be removed before use in taking the actual measurement.

U.S. Pat. Nos. 3,742,594 to Kleinberg, 3,926,766 to Niedrach et al and 4,561,963 to Owen et al, disclose the use of metal electrodes for electrochemical determination of various bodily fluids. All of these systems utilize wire probes, as opposed to planar structures, which are not conducive to the use of chemical pastes as thin films such as those used in the present invention. Further, these electrodes require liquid tight seals making their manufacture very difficult.

U.S. Pat. No. 4,545,382 to Higgins et al discloses a metal electrode coated with a film of glucose oxidase This system, however, utilizes a single sensor electrode, and is incapable of effecting a pH measurement U.S. Pat. Nos. 4,272,245 and 4,342,964 to Diamond et al disclose an apparatus and method for measuring the pH value of a blood sample which utilizes metal electrodes. This method, however, requires the presence of a liquid electrolyte used to calibrate the system and to provide an electrolytic bridge between the sample and the reference electrode within a cassette. Calibration does not occur automatically but, rather, the solution is introduced into the cassette by mechanical manipulation. Such solutions are heat sensitive and therefore must be stored refrigerated. The electrolyte-containing cassette must be heated to 37 degrees celsius prior to use as pH is a function of the temperature of the sample to be measured. After heating, the cassette has a shelf life of approximately one hour. A pH measurement using this method therefore requires proper treatment of the cassette containing the electrolyte before an accurate value can be determined. This can create unwanted delay in emergency situations. Additionally, the apparatus is designed to accommodate only one cassette at a time. Subsequent samples must be loaded into the machine manually and the user must wait a given amount of time before an accurate measurement can be made, thus causing an additional delay in critical circumstances. Further, a reading can only be taken when the cassette is in an upright position. Moreover, the measuring instrument which embodies the subject matter of these patents is large, table-top size, and requires a line source of power in order to perform the heating, measuring and other functions.

A further difficulty is encountered in blood gas measurement systems. Where an electrode system is used in which a measurement circuit is positioned in and out of contact with the electrode system, good, low ohmic contact is difficult to achieve. This is because the electrodes provide signals having a very large source resistance. As such, there is insufficient current flow to produce good low ohmic contact between the electrode system and the measurement circuit. The physics of this is that even with sliding gold contact surfaces there is always a surface layer which will provide some insulation. When working at very high circuit impedances, this layer is sufficient to degrade voltage measurement.

OBJECTS AND SUMMARY OF THE INVENTION

Accordingly, it is an object of the present invention to provide an inexpensive, portable apparatus for accurately measuring and reporting a blood gas panel, including pH levels, in whole blood to be used by paramedics, nurses, physicians and other practitioners.

It is another object of this invention to provide a system for pH measurement whereby the user need never come in direct contact with the blood sample to be measured.

It is a further object of the subject invention to permit a blood gas panel, including pH measurement, to be taken from a minimal quantity of blood.

It is another object of the present invention to provide a system for pH measurement which permits an in-situ calibration without mechanical manipulation and which requires no special storage nor heat treatment of the chemicals or sample prior to measurement.

It is still another object of the present invention to provide an interface between the electrode system and the measurement circuitry which will permit good ohmic contact to be obtained there between.

These and other objects are accomplished by way of a portable apparatus designed to accept a multiplicity of cartridges, each containing a measuring structure. One of the cartridges is then advanced into position within the apparatus. The apparatus then goes through a series of operational tests upon the positioned cartridge. The measuring structure is automatically calibrated and a temperature measurement is taken. If all readings are within the normal range, the apparatus prompts the user and a sample to be measured or analyzed is introduced into the cartridge. The cartridge is ejected following the determination of a blood gas panel, such as a pH value. In this way, the user need never come in contact with the blood sample being measured.

According to another aspect of the present invention, a blood sample is introduced into a disposable cartridge and drawn through a series of interconnected flow chambers including a sample chamber. The chambers downstream of the sample chambers act as overflow chambers to take up excess of the sample. Positioned within the sample chamber is a substrate upon which pH measuring means and thermal sensing means are disposed. It is a feature of this invention that the contents of the cartridge need not be heated prior to pH determination since a liquid electrolyte is not used and since the thermal sensing means functions to measure the actual temperature in-situ, at the time of calibration and of analysis, and automatically corrects the reading to a standard temperature, as preferred by medical personnel.

pH determination is accomplished by an electrode system which has a structure that is adaptable for use in determination of other blood parameters in a blood gas panel such as $O_2$, $CO_2$, etc. A multiplicity of electrodes, each adapted for measuring a different gas, can therefore be used to measure a full blood gas panel. In accordance with the present invention, the electrodes are substantially miniature planar structures. As such, all the necessary electrodes may be positioned within a single sample measuring chamber.

The electrode system is formed on a double-sided printed circuit board substrate. One side of the printed circuit board includes a plurality of gold-coated pads for making electrical contact between the substrate and a compatible pH analyzer. Copper traces on the other side of the circuit board form miniature, substantially planar structures upon which are formed an indicating and a reference electrode. The indicating electrode is coated with a metal or metal-metal oxide combination capable of developing a stable potential when in contact with an electrolyte.

In the preferred embodiment, the reference electrode is formed from a suitable metal-metal halide combination such that a stable potential is established when in contact with an electrolyte.

The electrodes are further coated with a thin film of a chemical paste thereby providing electrochemical contact between the indicating and reference electrodes. Alternatively, the chemical coating can be applied in two steps such that a thin film of paste is coated around the reference electrode and an indicator paste is coated as a thin film to surround the indicating electrode and the chemical paste in contact with the reference electrode.

An important aspect of the present invention is that the chemical pastes perform a dual function; that is the pastes are employed in both the calibration of the electrodes and in the measurement of the sample. In other words, unlike other electrode systems, the electrodes of the present invention need not have their calibrating medium cleared from them prior to actual measurement operation.

It is a feature of this invention that the formation of the electrodes as planar structures allows for the use of thin films of chemical and indicating pastes. The chemical compositions of the pastes permit storage of the electrodes in electrochemical contact and thus automatic calibration can take place immediately prior to sample injection without any prior hydration or user manipulation. Further, the cartridge containing the above described electrode structure can be stored at room temperature and need not be refrigerated to preserve the reactivity of the chemicals.

In the present invention, good ohmic contact is achieved between the electrode structure and the measurement electronics by way of means for isolated and non isolated generating currents which will flow through the electrode contact pads.

Further objects and advantages of the subject invention will become apparent from the following detailed description when taken in conjunction with the drawings.

DETAILED DESCRIPTION OF THE PREFERRED EMBODIMENTS

Figure 1:
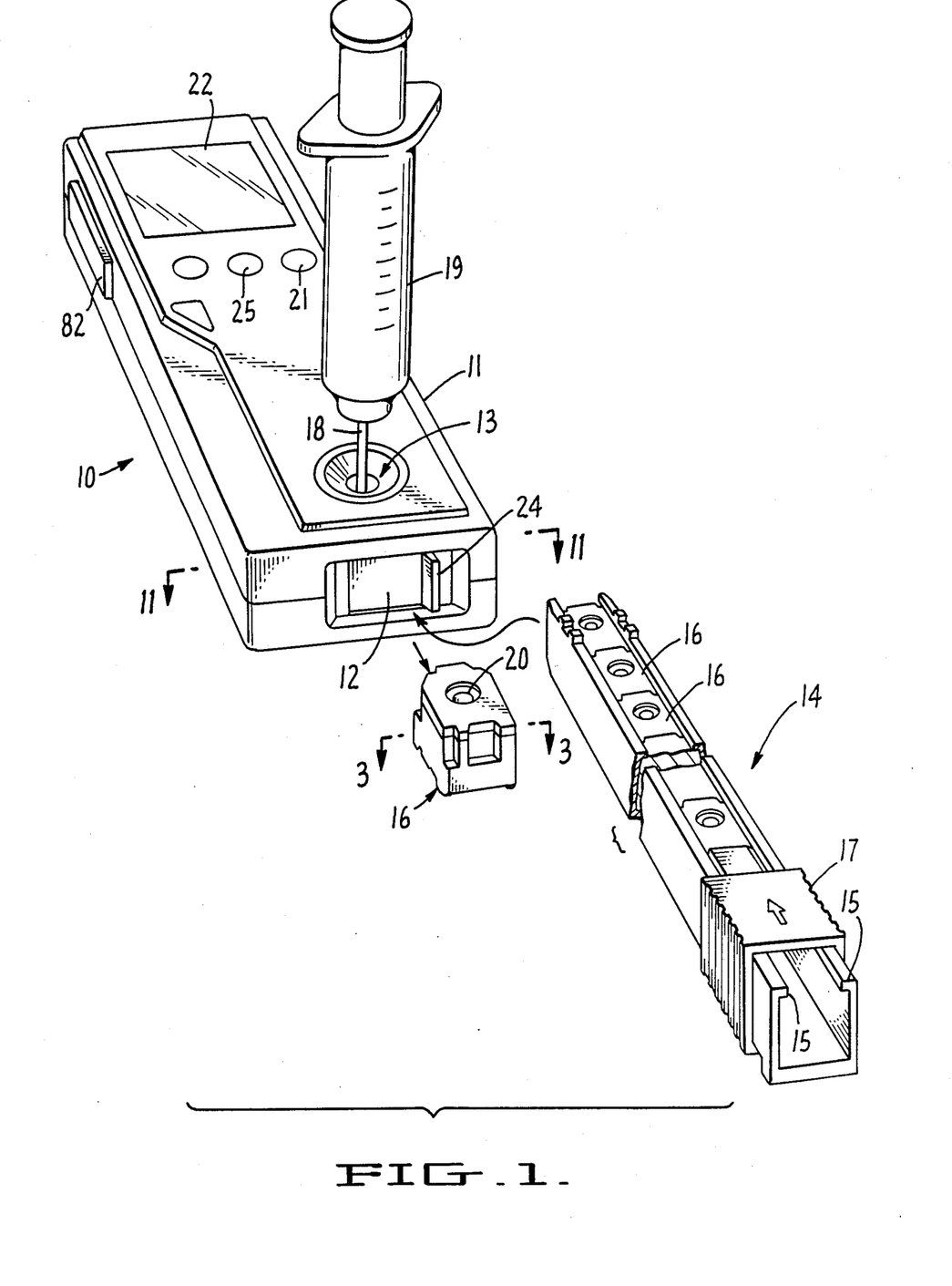
FIG. 1 is a perspective view of the portable apparatus according to the present invention.
Figure 2:
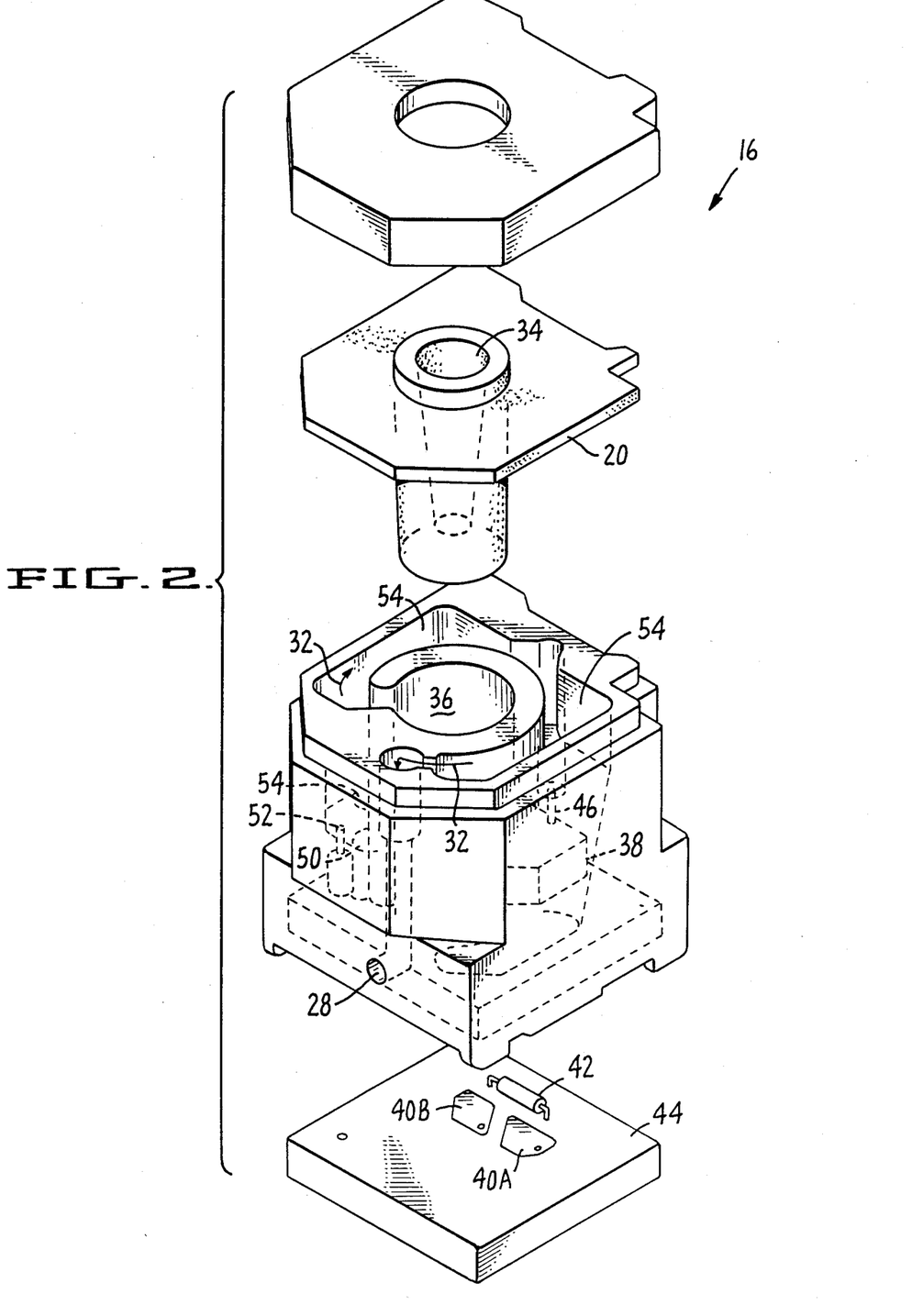
FIG. 2 is an exploded view of the preferred embodiment of a disposable cartridge according to the instant invention.

Referring now to FIG. 1, a portable pH measuring apparatus 10 is illustrated. The pH measuring apparatus includes a shell 11 which houses a cartridge bay 12 designed to receive a plurality of cartridges. The plurality of cartridges are loaded into apparatus 10 by way of U-shaped clip 14. New cartridges 16 are manually loaded onto the U-shaped clip 14. Clip 14 possesses longitudinal lips 15 to secure the cartridges 16. Subsequent cartridges 16 are loaded onto the clip 14 until it is either full or the desired number of cartridges have been loaded. A sleeve 17 provides a finger grip so that the clip 14 can be manually loaded into the cartridge bay 12. The sleeve 17 also acts as a barrier to ensure proper insertion of the new cartridges within the pH measuring apparatus 10. Sleeve 17 is somewhat larger in overall dimensions than the cartridge bay 12.

Figures 11, 12:
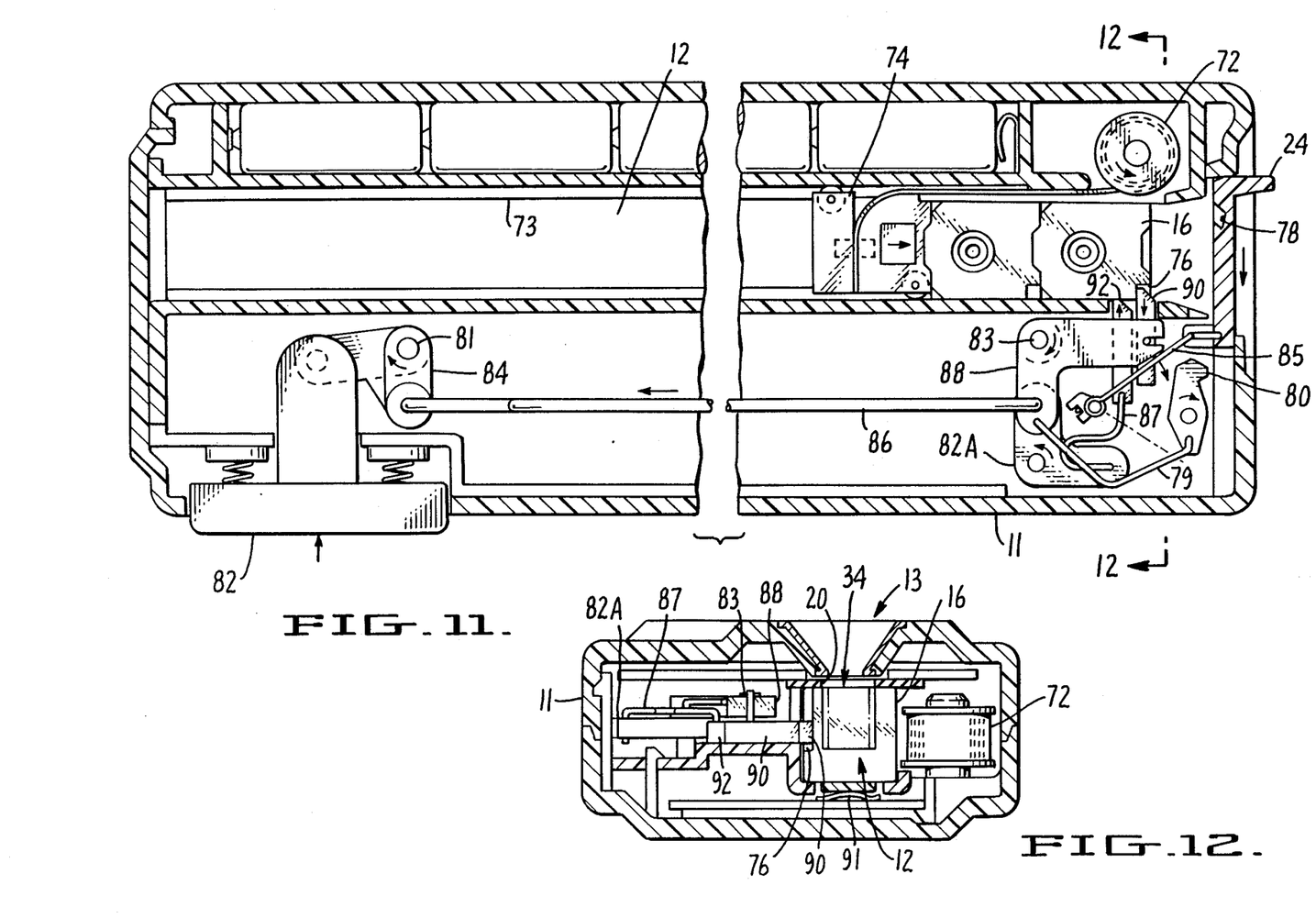
FIG. 11 is a cross sectional plan view of the portable pH measuring apparatus according to the present invention.
FIG. 12 is a cut away end view along the lines 12—12 of FIG. 11.

More specifically, as illustrated in FIGS. 11 and 12, as the clip 14 enters the cartridge bay 12, it contacts a cartridge follower block 74. A constant force spring 72, such as model no. CF015-0050 from Associated Spring, Cerritos, CA. is inserted and pinned at one end to the cartridge follower block 74. The other end of spring 72 is anchored to the shell 11 so that spring 72 becomes loaded as the follower block 74 is forced backwards along channel 73 by the entering clip 14. When the sleeve 17 contacts the outer edges of the shell 11, the clip 14 is removed and discarded. As clip 14 is withdrawn, a reciprocating projection 90, which was depressed downward by the cartridge clip 14, lifts and engages with a capturing groove 76 of the cartridge 16. The cartridges 16 are now in place within the cartridge bay 12 and measurement can commence. The cartridge 16 which is in the measurement position below a sample input port 13, has an electrical contact established between it and the apparatus 10.

The apparatus 10 further includes a cartridge counting mechanism (not shown) which keeps track of the number of cartridges present in the cartridge bay 12. This number is provided to the user by way of a visual display described herein below.

The portable pH measuring apparatus 10 is turned on via an on/off button (not shown) located on the apparatus 10. The apparatus 10 then conducts a series of automatic, self-diagnostic tests to ensure its proper operation. If everything is in order, the measuring structures are calibrated automatically, without any operator manipulation, as described in further detail below, and a temperature measurement is taken. If the measurements taken during the self-diagnostic tests are outside the normal range, a readout 22, FIG. 1, preferably a liquid crystal display, will instruct the user to discard the cartridge and a new cartridge can be inserted and the above steps repeated.

Figure 4:
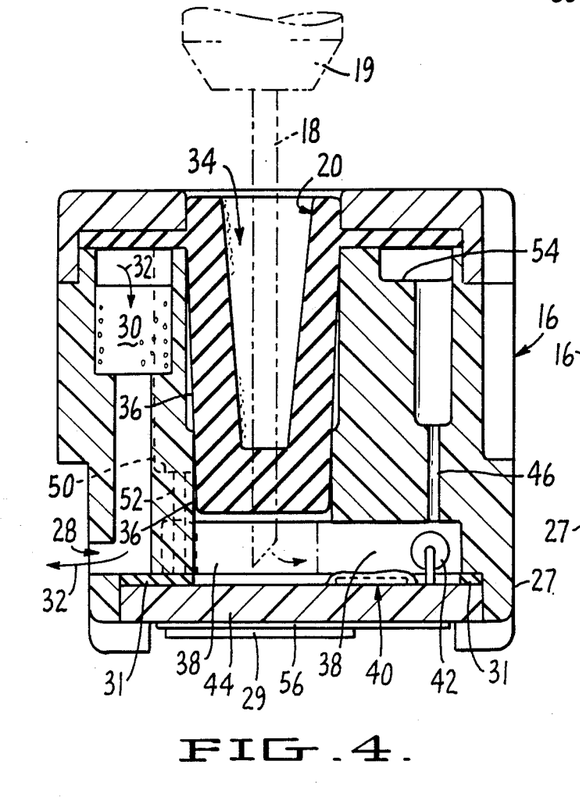
FIG. 4 is a cross sectional view along the lines 4—4 of FIG. 3.

When the cartridge is validated, the values are stored in memory and the readout 22 will so inform the user and a sample can then be inserted into the cartridge 16. As shown in FIGS. 1 and 4, the needle of a syringe 18 containing a blood sample to be measured is than passed through a shell hole (sample input port 13) and then inserted through a top seal 20 in the cartridge 16 and the blood sample is then dispensed into the cartridge 16.

A venous selection button 21, and arterial selection button 25, located on the face of the apparatus 10, allows the user to set the instrument for use with arterial or venous blood samples. In operation, the readings are calculated as arterial and a conversion factor is applied if the instrument is in the venous mode. The pH is determined potentiometrically, the temperature correction is calculated and a value corresponding to the pH of the measured sample is corrected to 37 degrees and displayed on the readout 22.

Referring now to FIGS. 11 and 12, the used cartridge can be ejected after a reading has been taken by pushing a spring actuated button 82 located on the apparatus 10. This causes a substantially L-shaped member 84 to rotate about a pin 81 in a clockwise direction thus drawing a push rod 86 towards the distal end of the apparatus 10. The drawing motion of the rod 86 applies a pulling force on "V"-shaped spring 79. This causes opposing projection 80 to pivot about a pin toward the proximate end of the shell 11. The user then pushes sideways on cartridge bay door 24 to engage notch 78 with opposing projection 80. This operates to maintain cartridge bay door 24 in an open position while the used cartridge is being ejected.

When the rod 86 is drawn towards the distal end of the apparatus 10, a bell crank 88 located in the proximal end of the apparatus 10 rotates in a clockwise direction about a pin 83. This motion forces the reciprocating projection 90 downward, thus freeing the used cartridge. The spring mounted cartridge follower block 74, which is biased by constant force spring 72 to apply force on the cartridges, is then permitted to move forward to forcefully eject the used cartridge out of the apparatus 10. This permits the used cartridge to be disposed of directly into a biohazard bin.

A bell-crank 82A is attached to another reciprocating projection 92 by means of a spring 87. As bell-crank 82A is rotated counterclockwise by movement of the push rod 86, the spring 87 pushes the projection 92 in an upward direction. This upward movement serves two purposes. First, the projection 92 applies a frictional force to the exiting cartridge so that the used cartridge is ejected in a controlled fashion. Additionally, the projection 92 captures the next cartridge by engaging with the capturing groove 76 on that cartridge. This prevents its exit. Once push button 82 is released, opposing projection 80 will rotate in a counterclockwise direction to release the cartridge bay door 24 into a closed position. Spring 85, which was loaded when cartridge bay door 24 was opened, supplies the return force to close the door.

When the eject button 82 is released, the ejection mechanism returns to its resting position as illustrated in FIG. 11. The reciprocating projection 92 moves downward and at the same time the other reciprocating projection 90 moves upward. Projection 90 thus exchanges position with projection 92 and catches the opposing groove 76 thus locking it into position so that a new pH measurement can be taken. This method of ejecting and advancing the cartridges eliminates the need for user contact with the blood-containing cartridge.

FIG. 12 is a cross sectional view of the invention taken along lines 12—12 in FIG. 1. There it can be seen that the cartridge 16, which is to receive a blood sample, is positioned in alignment with a sample input port 13. As shown, in this alignment, needle guideway 34 is positioned beneath sample input port 13.

As further illustrated in FIGS. 2-6, the disposable cartridge 16 includes a box-shaped housing 27 preferably composed of a static conductive material such as a carbon filled polymer, to bleed off the static charge that might be accumulated on the cartridge to the atmosphere. The top seal 20 of the disposable cartridge 16 is composed of a resilient material, such as but not limited to a silicone polymer. The top seal 20 operates in conjunction with a terminal air bleed port 28 to maintain a fluid-tight environment within the cartridge 16.

The terminal air bleed port 28 contains a submicron filter 30, preferably hydrophobic in nature. The submicron filter 30 is designed to provide a pressure differential between the cartridge 16 and the outside environment such that under static conditions the pressure differential threshold across the filter 30 is high and impedes the free flow of air in and out of the cartridge 16. When the sample is injected, air pressure builds. Thus, as the sample to be measured enters the cartridge 16, air within the cartridge is displaced and forced out of the terminal air bleed port 28 causing a directional flow of the sample through a series of interconnected flow chambers, housed within cartridge 16. These form a flow path, indicated by arrows 32.

Figure 5:
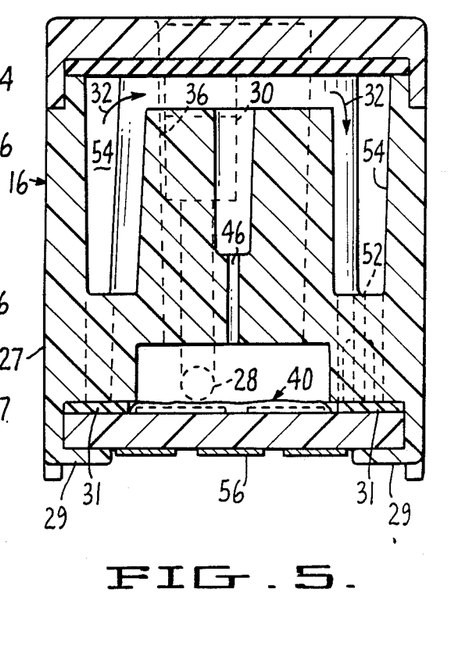
FIG. 5 is a cross sectional view along the lines 5—5 of FIG. 3.
Figure 6:
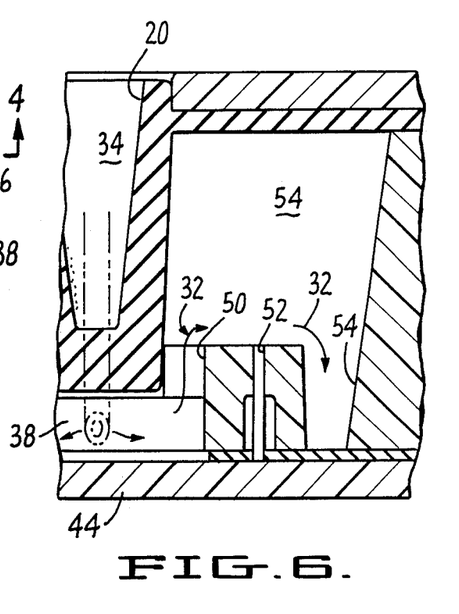
FIG. 6 is a fragmentary cross sectional view along lines 6—6 of FIG. 3.

More specifically, a needle 18, attached to a syringe 19 containing the blood sample to be measured, enters a longitudinally extending needle guideway 34, and pierces the top seal 20. As illustrated in FIGS. 4-6, the needle guideway 34 is bounded by walls 36, formed in top seal 20, which serve as guides to direct the needle towards the sample chamber 38. The needle guideway 34 is offset from a measuring structure 40 and thermal sensor 42 which are disposed on a printed circuit board substrate 44. The printed circuit board substrate 44 forms the bottom boundary of the sample chamber 38, See FIG. 2, and is approximately of the dimensions 0.625 inches×0.625 inches×0.625 inches. This configuration prevents the needle 18 from contacting and damaging the measuring structure 40 and thermal sensor 42. The circuit board substrate 44 also provides a barrier which prevents the needle from exiting the cartridge 16 through the bottom. Circuit board substrate 44 is held in place relative to the bottom of box-shaped housing 27 by way of fingers 29. See FIGS. 4 and 5. In the manufacturing process, these fingers 29 are initially formed as part of the side walls of the box-shaped housing 27, and then heat-deformed after the circuit board substrate 44 is positioned against the bottom of the box-shaped housing 27. A gasket 31 is positioned between the circuit board substrate and the bottom of box-shaped housing 27 to form a seal.

The blood sample is dispensed from the syringe 19 after the needle 18 has passed through the needle guideway 34 and into the sample chamber 38. Blood then flows into the sample chamber 38. The sample chamber 38 has a depth dimension that is positioned along the longitudinal axis of the needle guideway 34. The sample chamber 38 extends transversely and outwardly with respect to its depth dimension. A capillary sized intermediate air bleed port 46 is located so that the measuring and thermal sensing structures are positioned between the point where the blood sample enters the sample chamber 38 and the location of the intermediate air bleed port 46. This positioning of the intermediate air bleed port 46 aids in the prevention of air bubble formation. Further, the intermediate air bleed port 46 allows air trapped in the sample chamber 38 to be exhausted so that blood will flow into the sample chamber 38 and over the measuring structure 40 and the thermal sensor 42. In this manner, the directional flow of blood onto the measuring structure 40 is achieved, and the sample chamber 38 filled at any attitude between 0 degrees horizontal to 90 degrees vertical in spite of the high surface tension of blood relative to the force of gravity.

Figure 3:
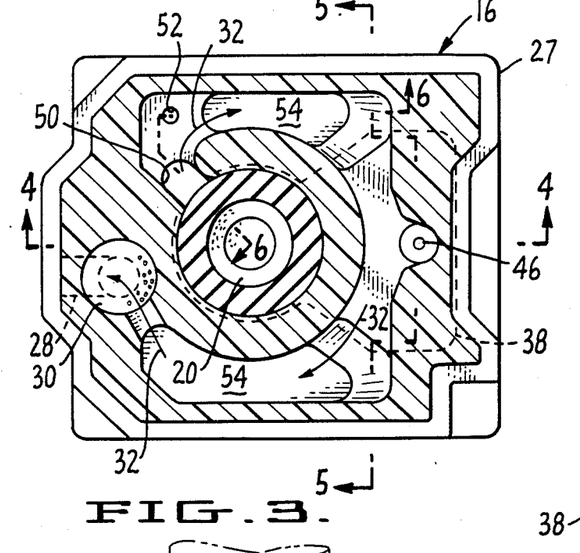
FIG. 3 is a top plan view of the disposable cartridge according to the instant invention

When the sample chamber 38 is full, blood flows through an overflow port 50, FIGS. 3 and 6, over a fill sensor 52, and into one of a series of overflow chambers 54 located substantially opposite the intermediate air bleed port 46. The presence of the overflow chambers 54 is desireable because only a minute quantity of blood is needed for pH determination and this small amount cannot be controllably dispensed by the user.

Since the size of the intermediate air bleed port 46 is very small in comparison to the overflow chambers 54, blood is held in the air bleed port 46 by capillary action and the high surface tension of the blood. Blood fills the overflow chambers 54 after the sample chamber 38 has been completely filled.

The overflow chambers 54 form a series of interconnected flow channels which surround the needle guideway 34 and sample chamber 38. When one of the overflow chambers 54 is full, blood spills into a pathway connecting the full chamber to an upstream overflow chamber.

This configuration of the interconnected flow chambers 32 permits use of the cartridge 16 in the apparatus 10 where the apparatus 10 is positioned in a continuous attitude of angles from horizontal to vertical. Thus, a reading can be taken when the apparatus 10 is hand-held and changing positions.

When the presence of a sample is detected by the fill sensor 52, the electronics of the apparatus 10 emits an audible signal and cuts the fill sensor 52 out of a common circuit shared by the measuring structure 40, the thermal sensor 42, and the fill sensor 52, thus allowing pH measurement to take place. Specifically, the impedance between the fill sensor 52 and the ground point 56B is measured by injecting a current 53 into point 56D, through the blood, and out of point 56B, and then measuring the voltage 55 which results between the points. See FIG. 10. When blood is present between the ground point 56B and the fill sensor 52, the measured impedance will be substantially low as compared to when the blood has not reached the level of the fill sensor 52. When blood has not yet reached this level, the impedance will be essentially infinity. There will be a difference in magnitude of impedance of at least 2 orders of magnitude when blood is present versus when blood is absent.

Figure 7:
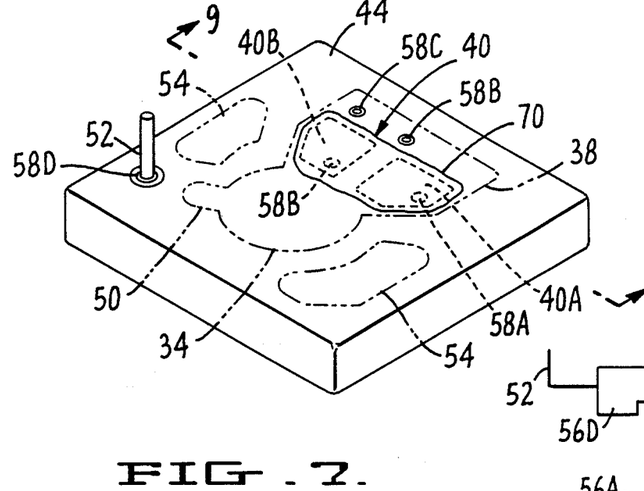
FIG. 7 is a perspective view of the preferred embodiment of the printed circuit board substrate of the present invention.
Figure 8:
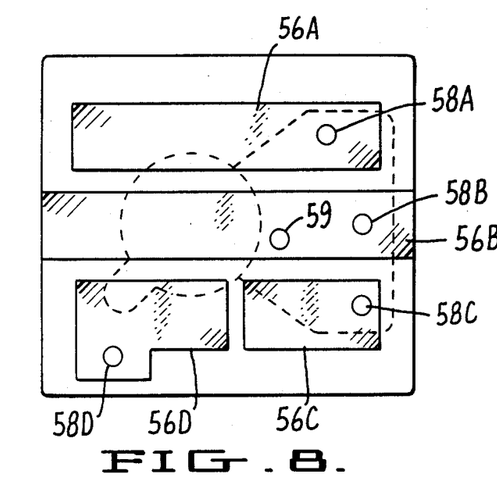
FIG. 8 is a bottom plan view of the preferred embodiment of the printed circuit board substrate of the instant invention.
Figure 9:
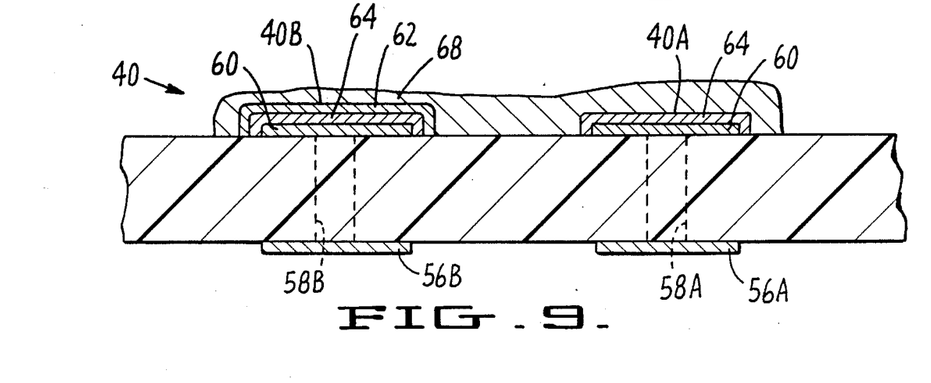
FIG. 9 is a cross sectional view along the lines 9—9 of FIG. 7.

Referring now to FIGS. 7-9, pH measurement is taken via the measuring structure 40 formed on a double sided printed circuit board substrate 44. The printed circuit board substrate 44 can be made from a reinforced polymer, such as an FR4 type phenolic epoxy. Other suitable materials include: reinforced paper, various molded polymers, reinforced or filled multipolymers, or any of the other standard types of printed circuit board substrates. These materials need not be smoothly planar and may be of a type such as three dimensional molded plastic, such as polyether sulfone. The printed circuit board includes a layer of copper on both sides which is etched by well known techniques to form electrical contact pads 56 on the outer surface and electrode base structures and thermal sensor mounting pads on the inner surface of the printed circuit board substrate 44.

In the preferred embodiment as illustrated in FIG. 8, four electrical contact pads 56A through 56D, with plated-through holes 58A through 58D, and 59, are present. A wire 52 is connected to contact pad 56D by way of feed-through 58D. Electrical contact pad 56B is longer than the others to ensure proper sequencing of power and ground to the measuring structure 40. The electrical contact pads 56A through 56D are designed to make contact with spring tensioned pads 91, FIG. 12, disposed in the portable pH apparatus 10 so that all the measurements can be effected.

The measuring structure 40, comprises an indicating electrode 40B and a reference electrode 40A, and is formed on the inner surface of the printed circuit board substrate 44. The underlying structure for these electrodes are pads of copper 60 formed by standard printed circuit board etching techniques. The use of printed circuit board technology as a foundation for the measuring means 40 provides a highly reproducible, low cost and high volume manufacturing technique.

Referring to FIG. 9, the copper pad 60 for the indicating electrode 40B is coated on all surfaces with a metal 62, preferably silver, then further coated with gold or platinum, or platinum group metals, or any other metal capable of developing a stable potential when in contact with an electrolyte. Alternatively, the indicating electrode can be formed from metal-metal oxide combination such as antimony layered over silver and further coated with antimony oxide. U.S. Pat. No. 3,742,594 to Kleinberg and U.S. Pat. No. 3,926,766 to Niedrach et al disclose the manner in which antimony electrodes can be formed.

The copper pad 60 for the reference electrode 40A is coated with a metal-metal halide combination such that a stable potential is established when the reference electrode 40A is in contact with an electrolyte. In the preferred embodiment, the reference electrode 40A is coated on all surfaces with silver 64 and further coated with silver chloride formed by anodic oxidation in dilute hydrochloric acid. Alternatively, the reference electrode 40A can consist of a calomel cell which is well known in the art.

In the preferred embodiment, the manufacturing sequence is as follows: (1) formation of the copper traces, including electrical contact traces on the outer surface, and electrode base structures and thermal sensor pads on the inner surface; (2) silver coating of all copper traces; and (3) gold over-coating of the silver-coated indicating electrode structure and the remaining conductive structures on the printed circuit board substrate 44, that is, everything except the reference electrode structure.

As illustrated in FIG. 9, the measuring structure 40 is coated with a thin film of a chemical paste 68 including a pH indicator, such as quinhydrone, a standard pH 7 buffer and a binder. It is to be understood that, although a pH 7 buffer has been used in the present example, other pH buffer values can be used as as well. If an antimony-antimony oxide cell is used, no additional indicator is necessary.

In an alternative embodiment of the present invention, the paste is coated in two steps such that a chemical paste, without a pH indicator, is first coated as a thin film to surround the reference electrode 40A and an indicator paste with a pH indicator is formed as a thin film to surround both the indicating electrode 40B and the chemical paste that is in contact with the reference electrode.

The overall construction of the measuring structure 40 allows for the use of a very small quantity of sample, as little as a few drops, since only the surface of the measuring structure 40 need be exposed to the sample to be measured Further, the nature of the chemicals used obviates the need for refrigeration to preserve the reactivity of the reagents and allows for automatic instrument calibration since the electrodes are stored in electrochemical contact.

The pH of the sample solution is determined by measuring the difference in electrical potential established between the reference electrode 40A and the indicating electrode 40B in the following manner. The quinhydrone is derived from an equimolar mixture of hydroquinone and quinone, which form an oxidation-reduction couple sensitive o pH. Hydroquinone is the reduced form of quinone. As known in the art, when a mixture of the two are in contact with an inert metal such as that used to form the indicator electrode 40B, the reaction can proceed in either direction as illustrated below.

$$QH_2 \rightleftharpoons Q + 2H^+ + 2e$$

The driving force of the reaction depends on the acidity and thus the pH of the solution in contact with the redox couple. Thus, a half-cell emf can be measured by the indicating electrode 40B when the redox couple is in contact with the chemical and indicator pastes described above versus the reference electrode 40A. This potential is compared to the potential established by the indicator and the reference electrodes when in contact with the pastes, prior to introduction of the sample, and a suitable mathematical formula is then used to determine the sample's pH value and stored in a microprocessor (not shown) in the portable pH apparatus 10.

Figure 10:
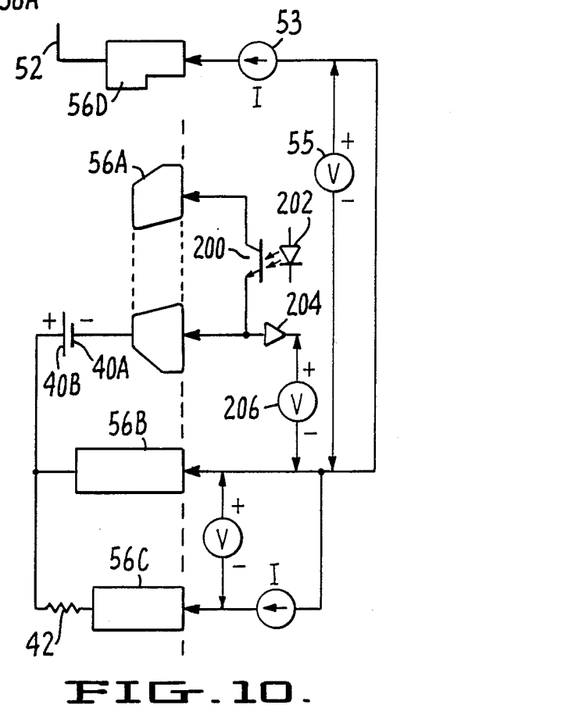
FIG. 10 is a schematic of the electrode, thermal sensor and fill sensor circuitry, and associated measurement electronics.

Referring to FIG. 10, the electrode potential is taken by measuring the voltage between pads 56A and 56B in the following manner. An instrumentation amplifier 204 is configured as a voltage follower, and its noninverting input is coupled to contact pad 56A. As described hereinbelow, an isolated current loop is formed using the collector and emitter of phototransistor 200 in contact with contact pad 56A at two spaced apart points. This forms what can be viewed as microwelds. Then, the isolated current loop is turned off. The instrumentation amplifier 204, connected to the emitter of phototransistor 200, can then take a measurement 206 of the electrode potential through a low ohmic contact. As can be seen from FIG. 10, this measurement is referenced to ground contact pad 56B.

Since pH is a function of temperature, the value determined above must be further corrected for any temperature variation. This is accomplished by the thermal sensor 42 which is located near the measuring structure 40 and disposed on the inner surface of the printed circuit board substrate 44 as illustrated in FIG. 4. The thermal sensor 42 is preferably constructed from a surface mount, or die, silicon thermistor. Due to its close proximity to the measuring structure 40, the thermal sensor 42 is able to accurately determine the pre-exposed temperature of the measuring structure 40, and the temperature of the blood sample undergoing measurement once the blood sample has been introduced into the sample chamber 38. The thermal sensor 42 is connected to a common contact point 56B which is shared by the indicating electrode 40B. See FIG. 10. A potential and temperature measurement can be taken sequentially and any variation in temperature can be corrected for by multiplying the obtained pH value by a blood temperature coefficient programmed in the microprocessor (not shown) within the portable pH analyzer 10. Similar corrections are made for each of the electrodes. Referring to FIG. 10, temperature is measured by injecting a current, I, between the thermal sensor contact 56C and the ground contact 56B and measuring the voltage, V, across the two contacts. The resistance, R, can then be determined according to the well known equation $R = V/I$.

As discussed briefly earlier in this disclosure, one of the problems encountered with high source impedance measuring circuits, such as the electrode system of the present invention, is that good ohmic contact between the electrodes and the measuring electronics is difficult to achieve. As can be seen in FIG. 12, as a cartridge 16 is advanced into position to receive a blood sample, pads 56A through 56D come into contact with corresponding spring loaded fingers 91. In the preferred embodiment of the present invention, the pads 56A through 56D and the spring loaded fingers 91 are gold plated. However, even with the use of sliding gold contact surfaces, as will be present when cartridge 16 is advanced into position, there still remains a surface layer which will provide some insulation. With the high source impedance signals that are sought to be measured, this layer of insulation is sufficient to degrade the measurement being taken.

In the present invention, the electrochemical cell parameters encountered makes it preferable that the measurement electronics have an input impedance of greater than $10^{12}$ ohms, and that leakage currents be controlled to be less than $10^{-12}$ amps. The output impedance of the cell itself can be on the order of $10^{11}$ ohms. As a consequence, capacitive loading at the measurement electronics should be strictly avoided.

As new cartridges 16 are positioned for receiving a blood sample, good ohmic contact can be achieved between the electrodes and the measurement electronics by running sufficient current through what is essentially a dry contact so that the contacts will in a sense microweld and provide a low resistance. It is to be understood that in "practice," electrical contact to the electrode cell is made by way of a contact pad. The measurement contacts are brought into physical contact with these contact pads and measure the voltage present at the contact pads.

Thus, in order to achieve good, low ohmic contact, a current should be generated which will flow from one of a pair of measurement contacts into and through the contact pad and back into the other of the measurement contacts. This should be isolated from all of the rest of the electronics. The generation of such current should be associated with but isolated from a control function which times or controls the value of the current used. In other words, an action-at-a-distance coupling is desireable. It is desirable to be able to control the current and turn it off so that once a good contact is made, there is not a voltage drop across the contact which might be caused by the generating current. Such a voltage drop would lead to unpredictable voltage offsets in the measurement.

There are several possible mechanisms for causing such current to flow in a predictable manner. For example, thermocouples could be placed on either side of the two contacts. One of them could be remotely heated. Unfortunately, the unusual metals involved could present uncontrolled thermoelectric currents. Further, such a system has a slow response time. Once heated, the thermocouple would have to cool and be maintained at the same temperature as the other thermocouple.

Another example is that the secondary of a transformer could be placed in the current loop. Current in the secondary could be induced by current in the primary of the transformer. While this configuration would be workable, the primary drive circuitry would be somewhat complex and the direction of current flow is not easily controlled.

As can be seen from FIG. 10, in the preferred embodiment of the present invention, a photo-diode or photo-transistor 200 is placed in the current loop. Light from an LED 202 or other source is turned on to cause current to flow in the photo-diode or photo transistor. The collector of transistor 200 is physically contacted with pad 56A at one point and the emitter of transistor 200 is physically contacted with pad 56A at a different spaced apart point. The driver circuit for the LED is a simple common emitter stage (not shown) which can use a PNP transistor, such as device number 2N2907. An optical isolator, such as device number 4N35, manufactured by Hewlett Packard of Palo Alto, CA. is readily available, and contains both a photo-transistor and an LED. With such a structure, the current flow is controllable in both magnitude and direction, and can be readily turned off. Further, there are no significant thermoelectric currents. In the preferred embodiment of the present invention, a current of approximately 50 to 100 microamps is caused to flow through transistor 200. In general, a current of two to three times the magnitude of the current sought to be measured should be used to form these low ohmic contacts.

It is now readily apparent that the instant invention provides a means for accurately determining all parameters associated with in-situ pH measurement of whole blood. Since the described apparatus is portable and requires a very small sample size, measurements can easily be taken in emergency situations by ambulance attendants and the like. The user need never come in contact with the blood sample being measured thus eliminating the dangers associated with such contact. It should be understood that while the subject invention has been disclosed with reference to a preferred embodiment, various alternatives to the unique concepts described herein may be employed in practicing the present invention. Thus, although the measuring structures and chemistry of the present invention have been disclosed with reference to pH measurement, alternative uses, such as the measurement of other blood gas parameters, can be envisioned using the present system. It is intended that the following claims define the invention, and that the structure within the scope of these claims and their equivalents be covered thereby.

What is claimed is:

1. A portable apparatus for measuring the electrochemical characteristics of a sample, said apparatus comprising:

a shell housing a cartridge bay configured so as to receive a plurality of cartridges from a clip;

spring loaded means for advancing one of the cartridges into a measurement position within said shell;

measuring structure means for measuring an electrochemical characteristic of a sample;

means for in situ, automatic calibration of the measuring structure means within the cartridge prior to introduction of the sample into the cartridge when said cartridge is in the measurement position;

means for indicating the electrochemical characteristics of the sample as measured by and received from the measuring structure means; and means for ejecting the cartridge holding the sample from the shell after information corresponding to the electrical characteristics of the sample has been indicated.

2. The portable apparatus of claim 1 wherein the cartridge bay of said shell comprises a linear channel capable of receiving a single file row of cartridges.

3. The portable apparatus of claim 1 wherein said spring loaded means comprises a loaded spring in contact with and delivering a constant force to and driving an unused cartridge into measurement position upon ejection of a used cartridge.

4. A portable apparatus for measuring the electrochemical characteristic of a sample, said apparatus comprising:

a shell housing a linearly channeled cartridge bay having a first end at a measurement position and a second end, the cartridge bay configured so as to receive a single file row of cartridges from a clip;

a loaded spring having a first end attached to said shell and a second end in contact with the cartridges in the second end of the cartridge bay, said spring delivering a force to the cartridges in the direction of the measurement position;

measuring structure means for measuring an electrochemical characteristic of a sample;

means for in situ, automatic calibration of said measuring structure means within the cartridge prior to introduction of the sample into the cartridge when said cartridge is in the measurement position;

means for indicating the electro-chemical characteristics of the sample as measured by and received from the measuring structure means; and means for ejecting the cartridge holding the sample from the apparatus after information corresponding to the electrical characteristics of the sample has been indicated.

* * * * *

UNITED STATES PATENT AND TRADEMARK OFFICE
CERTIFICATE OF CORRECTION

PATENT NO. : 4,929,426

DATED : May 29, 1990

INVENTOR(S) : Bodai et al.

It is certified that error appears in the above-identified patent and that said Letters Patent is hereby corrected as shown below:

In column 9, line 62, a period (".") should follow the word "measured"; and

In column 10, line 5, insert the letter "t" before "o" to make the word "to".

Signed and Sealed this

Twelfth Day of November, 1991

Attest:

HARRY F. MANBECK, JR.

*Attesting Officer*  *Commissioner of Patents and Trademarks*